United States Patent [19]

Swihart

[11] Patent Number: 4,587,320

[45] Date of Patent: May 6, 1986

[54] METHOD FOR MAKING CARBOXYFUNCTIONAL SILICONE GLYCOLS

[75] Inventor: Terence J. Swihart, Essexville, Mich.

[73] Assignee: Dow Corning Corporation, Midland, Mich.

[21] Appl. No.: 684,995

[22] Filed: Dec. 21, 1984

[51] Int. Cl.$^4$ ............................................. C08G 77/04
[52] U.S. Cl. ....................................... 528/23; 528/30; 528/37; 556/439; 556/462
[58] Field of Search ............................ 528/23, 30, 37; 556/462, 439

[56] References Cited

U.S. PATENT DOCUMENTS 3,965,150  6/1976  Moeller ................................ 556/439
4,081,410  3/1978  Moeller ................................ 556/439

*Primary Examiner*—Melvyn I. Marquis
*Attorney, Agent, or Firm*—George A. Grindahl

[57] ABSTRACT

Carboxyfunctional silicone glycols are made by equilibration at elevated temperatures of silicone glycols in which the glycol radical or radicals are bonded to silicon with an Si—C linkage and carboxyfunctional siloxanes in which the carboxy radical or radicals are bonded to silicon with an Si—C linkage in the presence of an acid catalyst which is capable of breaking Si—O linkages but not Si—C linkages. The carboxyfunctional silicone glycols so produced are of the type which are useful as profoamers, surfactants, spreading agents for active chemicals, such as pesticides, hydrophilizing treatments for fabrics and hair, as emollients in cosmetic formulations and as chelates.

19 Claims, No Drawings

METHOD FOR MAKING CARBOXYFUNCTIONAL SILICONE GLYCOLS

FIELD OF THE INVENTION

This invention relates generally to carboxyfunctional silicone glycols and more specifically to a novel method for making said glycols.

PRIOR ART

Carboxyfunctional silicone glycols are not new. They are known from, for example, U.S. Pat. No. 4,336,001 to Ona et al, issued on Dec. 28, 1982. This U.S. patent describes a carboxyfunctional siloxane, which may be a silicone glycol, for use in a system of components which are crosslinked after application to fibers. Such carboxyfunctional silicone glycols are also disclosed in U.S. Pat. No. 4,359,545, issued Nov. 16, 1982, to Ona et al and U.S. Pat. No. 4,459,382, issued July 10, 1984 to Ona.

The siloxane described in the Ona et al '001 patent may be produced by the addition reaction specified in U.S. Pat. No. 2,970,150, issued on Jan. 31, 1961, to Bailey. The Bailey patent discloses a process wherein siloxanes having one or more silicon-to-hydrogen bonds can be added to unsaturated organic compounds in the presence of a platinum catalyst to provide siloxane adducts containing silicon bonded hydrocarbons, or silicon bonded hydrocarbons containing functional substituents (such as alcohols and carboxyls).

There are certain difficulties, however, with the prior art method of making such materials. One such difficulty is that it is possible in the prior art method to experience a reverse addition reaction so that the products are vinyl acetoxy radicals on silicon, and hydrogen. The vinyl acetoxy radical can react with Si—H linkages in the reaction mixture to result in crosslinking. This is considered to be a problem of the prior art.

It is another difficulty of the prior art that sulfur containing carboxyfunctional radicals cannot normally be used in a platinum catalyzed system because the sulfur will poison the catalyst. Sulfur containing carboxyfunctional radicals are often desirable in such materials when they are intended to be used in chelation or complexation operations, such as coal flotation. This is also considered to be a problem of the prior art.

It is another problem of the prior art method that it is sometimes difficult to get a complete reaction of the Si—H linkages, and a resulting instability in the reaction product is observed as Si—H linkages continue to react with carboxyfunctional groups to produce $H_2$ and Si—OOC—RSi. The instability is noticeable in the viscosity of the reaction product.

In the prior art method of making carboxyfunctional silicone glycol it is a problem that the Si—H addition reaction may be unpredictable when reactants of differing kinetic reactivity are added. Reactants with a higher kinetic reactivity will preferentially react with the majority of Si—H sites. This creates difficulties when a homogeneous terpolymer is desired.

SUMMARY OF THE INVENTION

It is therefore an object of the present invention to overcome the disadvantages and problems of the prior art.

It is also an object of the present invention to present an improved method for making carboxyfunctional silicone glycols.

These and other objects are accomplished by a method for making a carboxyfunctional silicone glycol which comprises, generally speaking, the steps of
(1) mixing together
(a) a silicone glycol or a mixture of silicone glycols in which at least one of the glycol radicals is bonded to silicon with an Si—C linkage;
(b) a carboxyfunctional siloxane, or a mixture of carboxyfunctional siloxanes in which at least one of the carboxy radicals is bonded to silicon with an Si—C linkage and wherein at least one of (a) and (b) also include non-glycol-containing and non-carboxyfunctional-containing diorganosiloxane units; and
(c) a catalytic amount of an acid catalyst capable of breaking Si—O linkages in (a) and (b) but not Si—C linkages therein;
(2) heating the mixture to an elevated temperature; and
(3) maintaining the mixture at said elevated temperature for at least about 4 hours, whereby equilibration of (a) and (b) occurs to produce an equilibration product containing carboxyfunctional silicone glycol.

The mixing and heating steps may be done simultaneously and subsequent optional steps of neutralizing the catalyst and filtering the reaction product may be employed. In yet another optional subsequent step, the carboxyfunctional radical of the carboxyfunctional silicone glycol can be reacted with metal hydroxides to form ionic salts.

DETAILED DESCRIPTION

It has been found that a carboxyfunctional silicone glycol can be formed by equilibrating certain silicone glycols and certain carboxyfunctional silicones at an elevated temperature in the presence of a catalytic amount of a strong acid catalyst. Distinguishing features of the present invention are that the acid catalyst be capable of breaking Si—O linkages but not Si—C linkages in the reactants and that the glycol radical and the carboxyfunctional radical, respectively, be bonded to silicon by Si—C linkages. Other features of the invention such as the various parameters relating to the specific nature and proportions of the reactants, alternative embodiments, uses of the product, and the like will be readily understood by those of ordinary skill in the silicone technology and in equilibration reactions once such distinguishing features are understood.

Generally speaking, useful silicone glycols (a) and carboxyfunctional siloxanes (b) are those which have Si—C linkage between the glycol or carboxy radicals and silicon. Such useful silicone glycols and carboxyfunctional siloxanes should also have glycol or carboxy radicals which will not interfere with the equilibration reaction or neutralize the acid catalyst. Typical of such useful silicone glycols (a) are those corresponding to general formulae (I) and (II) while general formulae (III) and (IV) are typical of useful carboxyfunctional siloxanes (b). These general formulae are:

(I)
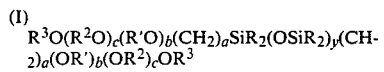

wherein each "R" is a substituted or unsubstituted hydrocarbon radical, "R'" is —CH$_2$CH$_2$—, "R$^2$" is "R'" or

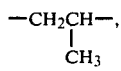

"R³" is hydrogen or a substituted or unsubstituted hydrocarbon radical, "a" is a positive integer, "b" plus "c", either of which may be zero, equal from about 1 to about 50, inclusive, and "y" is a positive integer.

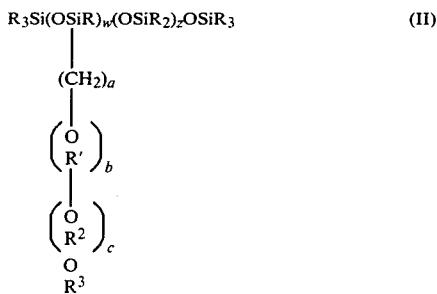

wherein "w" and "z" are positive integers and "R", "R'", "R²", "R³", "a", "b" and "c" are as described in connection with general formula (I).

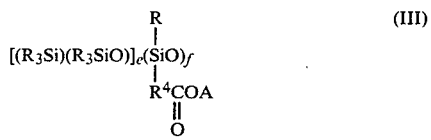

wherein "R" is a radical as described in connection with formula (I), "R⁴" is any divalent hydrocarbon radical or hetero-atom-containing hydrocarbon radical which provides Si—C linkage, "A" is hydrogen or any monovalent substituted or unsubstituted hydrocarbon radical, "e" is 1 or 0, "f" is 3 to 6, inclusive, when "e" is 0, and "f" is a positive integer when "e" is 1.

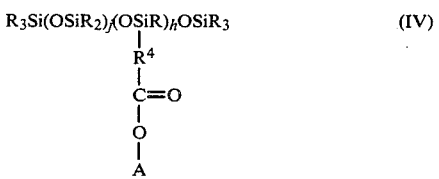

wherein "R" is a radical as described in connection with formula (I), "R⁴" and "A" are as described in connection with formula (III) and "j" and "h" are positive integers.

In connection with formulae (I), (II), (III) and (IV) good results have been observed when "R" is methyl. It will be readily understood by those of ordinary skill in the silicone technology that each "R" may also normally be other substituted or unsubstituted hydrocarbon radicals such as ethyl, propyl, trifluoropropyl, and the like. It will also be readily understood by those of such skill that although the phenyl radical may sometimes be useful it may also demonstrate some instability in the presence of the preferred acid catalyst, described below. It is generally preferred that "R" is methyl due to cost and availability considerations.

In connection with formula (I), good results have been obtained using a readily available embodiment wherein "y" is 14 to 15 and when all "R's" are methyl. It will be appreciated by those of ordinary skill in the silicone technology that "y" can vary greatly depending on the desired viscosity of the equilibration product. When a liquid product is desired "y" can be a very low value (from about 10 to about 500) and when a gum-like product is desired "y" can be a higher value (up to about 5,000).

In connection with formulae (I) and (II), although "a" can be any positive integer, the readily available propylene radical, where "a" is 3, has been used with good results. Good results have also been obtained when values for "b"+"c" equal about 24 and also when "b" is equal to 12 and "c" is equal to 0.

In formulae (I) and (II), "R³" is typically hydrogen. It will be readily apparent, however, to those of ordinary skill in the silicone technology that "R³" could also be, for example, a methyl, ethyl, propyl or trifluoropropyl radical when the glycol is ether capped. It will also be readily understood by those of such skill that "R³" could be

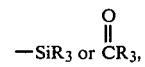

wherein "R" is as described above.

The value of "z" in formula (II) may vary greatly depending on such factors as the desired viscosity of the equilibration product as in connection with "y" of formula (I). For example, when a liquid product is desired, "z" will typically be from about 10 to about 500. However when a gum-like product is desired "z" may be as much as 5000.

The value of "w" in formula (II) may also vary greatly depending on the glycol substitution in the siloxane polymer. In the silicone industry silicone glycols are typically available where "w" varies from about 1 to about 10, and all such materials are useful in the present invention.

In connection with formula (III), good results have been obtained when "R⁴" is —SCH₂—, although "R⁴" may be any divalent hydrocarbon or hetero-atom-containing divalent hydrocarbon radical.

In formula (III) "A" can be hydrogen or any substituted or unsubstituted hydrocarbon radical which will not interfer with the equilibration reaction or neutralize the catalyst. Good results have been obtained when "A" is hydrogen, and "A" should be hydrogen when the subsequent additional step of treating the equilibration product with a metal hydride is anticipated. However, "A" can also be, for example, methyl, ethyl, or propyl.

In formula (III) "e" can be 1 or 0. If "e" is 0, the carboxyfunctional siloxane will be a cyclic siloxane and "f" will range from about 3 to about 6. However, when "e" is 1, the siloxane will be linear and "f" will be a positive integer. Linear such carboxyfunctional siloxanes are normally available in embodiments where "f" is from about 1 to about 10, and all such materials are useful in the present invention. Cyclic carboxyfunctional siloxanes are preferred, however, due to cost and availability considerations.

In formula (III) "R" is as described in connection with formula (I).

In the carboxyfunctional siloxane of formula (IV) "R" is as described in connection with formula (I) and "R⁴" and "A" are as described in connection with formula (III). In formula (IV) "j" may be any positive integer but is normally selected depending on the desired viscosity of the equilibration product. When the equilibration product is desired to be a liquid, "j" is typically from about 10 to about 50 and may be as high as 5000 when a gum-like product is desired.

Carboxyfunctional siloxanes which correspond to formula (IV) are typically available in embodiments where "h" ranges from 1 to 25, and all such materials are useful in the present invention.

The acid catalyst (c) may be any acid strong enough to break the Si—O bonds in (a) and (b) and allow rearranging of the polymers, but not strong enough to break Si—C bonds. Useful catalysts include, for example, sulfuric acid, trifluoromethane sulfonic acid and clays treated with trifluoromethane sulfonic acid. Sulfuric acid is not preferred because it is sufficiently strong to also oxidize radicals which might sometimes be attached to the siloxane polymer chains. In some cases this would be undesirable. Trifluoromethane sulfonic acid is preferred in concentrations of about 200 parts per million (ppm) to effect equilibration within a reasonable period of time.

It will be clear to one of ordinary skill in the silicone technology that the relative proportions of the silicone glycol radicals and the carboxyfunctional siloxane radicals in the equilibration reaction will have an effect on the nature of the equilibration product. It is possible to use a sufficiently small amount of the carboxyfunctional radicals that not every molecule in the equilibration product will be a carboxyfunctional silicone glycol. Such equilibration products are often useful and are intended to be within the scope of the invention. Likewise, it is possible to obtain a useful equilibration product by loading the equilibration mixture with a high percentage of carboxyfunctional siloxane radicals so that the reaction product is also heavily loaded with carboxyfunctional radicals. Such useful carboxyfunctional silicone glycols made by the method of the present invention can be described in terms of molar relationships between carboxyfunctional siloxane units, silicone glycol units and diorganosiloxane units. ["Diorganosiloxane units" shall be understood to mean non-glycol-containing and non-carboxyfunctional-radical-containing such units. Such units are exemplified by units "y" in general formula (I)]. Useful carboxyfunctional silicone glycols typically have between about 0.5 and about 20 mole percent of carboxyfunctional siloxane units and between about 0.5 and about 20 mole percent of silicone glycol units with the remainder being substantially diorganosiloxane units but sometimes including triorgano-endblocking units such as is shown in general formula (VI), below.

The order of mixing the components is not critical. Normally the carboxyfunctional siloxane is added to the silicone glycol to form a first mixture and the acid catalyst is added to the first mixture to form a second mixture. Of course, mixing is done in a reaction vessel which will not be attacked by the acid catalyst.

The second mixture is then heated to an elevated temperature and the elevated temperature is maintained until equilibration is substantially achieved. The mixing and the heating of the mixture may occur simultaneously without adverse effect in order to shorten the manufacturing cycle.

The equilibration reaction mixture is heated to an elevated temperature to speed the reaction. The degree of heating depends on the catalyst used. For example, when the catalyst is sulfuric acid or sulfonic-acid-treated clays, the equilibration is observed to proceed better at temperatures above about 90° C. However, when the preferred catalyst is used, as described above, the equilibration has been found to proceed better at temperatures between about 40° C. and about 65° C. Within these temperature ranges the equilibration generally is observed to require at least about four hours, but not normally longer than about 16 hours.

As an optional, subsequent step in the present novel method of making carboxyfunctional silicone glycols, the catalyst may be neutralized. For example, as will be appreciated by those of ordinary skill in the silicone technology, a trifluoromethane sulfonic acid catalyst may be neutralized by treating the reaction mixture with dimethyl formamid. In a further optional, subsequent step the equilibration reaction product may be filtered to remove the salts formed during neutralization.

Another optional, subsequent step to the equilibration reaction is the treatment of the equilibration product with a metal hydroxide, such as potassium hydroxide or sodium hydroxide. This optional subsequent step is useful when "A" is hydrogen in formulae (III) and (IV) shown above. The effect of the treatment is to change the carboxyfunctional radical to —COO$^-$Na$^+$ or to —COO$^-$K$^+$, as will be readily appreciated by those of ordinary skill in the silicone technology.

The carboxyfunctional silicone glycols in the equilibration product are useful for example, as profoamers, surfactants, spreading agents for active chemicals, such as pesticides, fabric treating agents to hydrophilize fabric and emollients in cosmetic formulations. The carboxyfunctional silicone glycols which have been subsequently treated with a metal hydroxide are preferred for fiber treatment and for use in cosmetic formulations because the ionic nature of the treated carboxyfunctional radical enhances the substantivity of the material on the surface of human or on treated fibers. The metal hydroxide treated equilibration product can also be used as a non-ionic/anionic surfactant.

Equilibration products according to the present invention in which $R^4$ contains a hetero atom, such as sulfur, are useful as chelating agents for applications such as coal flotation.

The general structural formula of the carboxyfunctional silicone glycol or glycols formed in the equilibration reaction will depend on whether the silicone glycols of formula (I) or (II) or a mixture thereof are used. Likewise the general structural formula of the resulting carboxyfunctional silicone glycol will also depend on whether the carboxyfunctional siloxane of formula (III) or (IV) or a mixture thereof is used.

The carboxyfunctional silicone glycols of the present invention will normally correspond to general formulae (V) or (VI) or will be mixtures thereof. General formulae (V) and (VI) are:

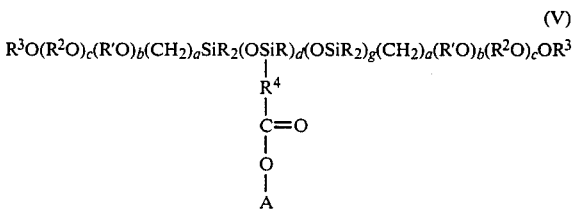

wherein "R", "R'", "R²", "R³", "R⁴", "a", "b", "c" and "A" are as defined above and wherein "d" and "g" are selected such that the carboxyfunctional siloxane units comprise from about 0.5 to about 20 mole percent of the molecule and the silicone glycol end units make up from about 0.5 to about 20 mole percent of the molecule.

$$R_3Si(OSiR_2)_i(OSiR)_k(OSiR)_lOSiR_3 \quad (VI)$$

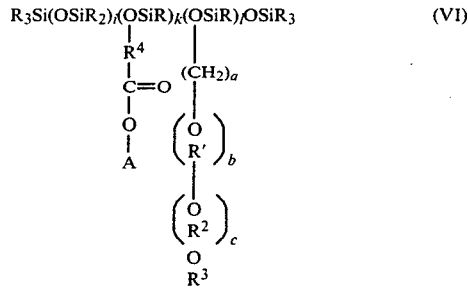

wherein "R":, "R'", "R²", "R³", "R⁴", "A", "a", "b", and "c" are as described above and "i", "l" and "k" are selected such that the carboxyfunctional siloxane units will make up from about 0.5 to about 20 mole percent of the molecule and the silicone glycol units make up from about 0.5 to about 20 mole percent of the molecule.

EXAMPLES

The invention is illuminated and exemplified by the following examples, which are not intended to be exhaustive.

EXAMPLE 1

To 50 grams (0.021 moles) of a silicone glycol having the general formula $$\text{H(OCH}_2\text{CH}_2)_{12}\text{O(CH}_2)_3\text{—Si}\overset{\text{Me}_2}{\underset{}{|}}\text{—(OSiMe}_2)(\text{CH}_2)_3(\text{OCH}_2\text{CH}_2)_{12}\text{—OH}$$

was added 3.8 grams (0.023 prime moles as $$\overset{\text{Me}}{\underset{}{\text{OSiCH}_2\text{CH}_2\text{SCH}_2\text{CO}_2\text{H})}}$$

of a cyclic carboxyfunctional siloxane having the formula $$\overset{\text{Me}}{\underset{}{[\text{OSiCH}_2\text{CH}_2\text{SCH}_2\text{CO}_2\text{H}]_4}}$$

in a 4 oz. bottle. To this was added 0.04 grams of trifluoromethane sulfonic acid.

This mixture was heated to 60° C. while standing in a sealed oven for 66 hours. The resulting equilibration product was clear and was soluble in water. When dissolved in water it functioned as a profoamer. There was no evidence of silicone oil on the surface of the water solution after the foam disappeared, indicating that the carboxyfunctional siloxane had reacted into the silicone glycol.

It will be well known to those of ordinary skill in the silicone technology that unreacted carboxyfunctional siloxane in the reaction product would not be soluble in water and would function as an antifoam therein.

Standard laboratory analysis of the equilibration product indicated that it had the structural formula

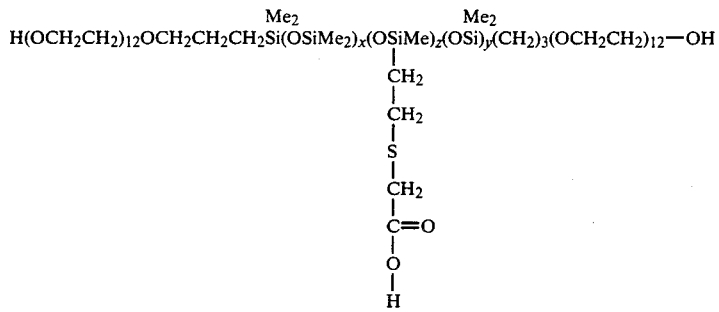

where $x+y=13$ to 15 and $z=1$.

This example indicates that a carboxyfunctional siloxane in which the carboxy radical is connected to silicon by an Si—C linkage and a silicone glycol in which the glycol radical is connected to silicon by an Si—C linkage can be equilibrated in the presence of an acid capable of breaking Si—O linkages but not Si—C linkages to produce a carboxyfunctional silicone glycol. From this example, it will be readily understood by those of ordinary skill in the silicone technology that other such silicone glycols and such carboxyfunctional siloxanes can be equilibrated in the presence of such an acid to form other carboxyfunctional silicone glycols within the scope of this invention. It will also be understood by those of such skill that the above-mentioned problems of the prior art are overcome in that the sulfur in the carboxyfunctional reactant does not interfere with the acid catalyst and in that Si—H linkages are avoided in the equilibration reaction.

EXAMPLE 2

This example demonstrates that carboxyfunctional silicone glycol according to general formula (V) can be made by the present inventive method in a variety of ratios of diorganosiloxane units, silicone glycol units and carboxyfunctional siloxane units, from starting materials according to general formulae (I) and (III).

Four samples were prepared having the general formula

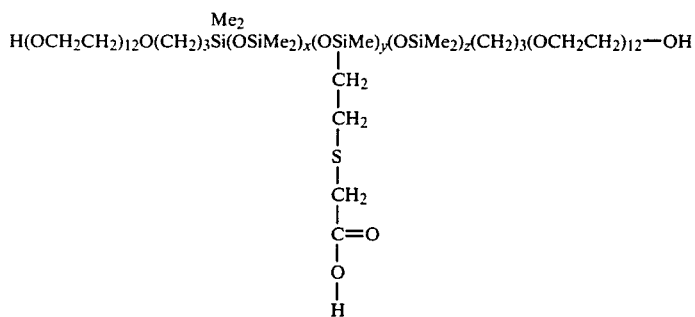

where "x"+"z" is 14 and where "y" has an average value as shown in Chart 2b.

The four samples were prepared by mixing the carboxyfunctional siloxane, the silicone glycol and the trifluoromethane sulfonic acid of Example 1 in the proportions set out in Chart 2a.

| | Chart 2A | | |
|---|---|---|---|
| Sample | Carboxyfunctional Siloxane | Silicone Glycol | Acid |
| 1 | 400 g | 9.3 g | 0.4 g |
| 2 | 400 g | 18.2 g | 0.4 g |
| 3 | 400 g | 36.0 g | 0.4 g |
| 4 | 400 g | 71.2 g | 0.4 g |

These ingredients were mixed in pint glass jars, sealed and placed in a 65° C. oven for 4 hours and allowed to equilibrate. The equilibration products had molar radios or components as set out in Chart 2b.

| | | Chart 2b | | |
|---|---|---|---|---|
| Sample | Avg. Value of "y" | Mole % Diorgano-siloxane | Mole % Carboxyfunctional Siloxane Units | Mole % Silicone Glycol Units |
| 1 | 0.3 | 85.89 | 1.84 | 12.27 |
| 2 | 0.6 | 84.34 | 3.61 | 12.05 |
| 3 | 1.2 | 81.39 | 6.98 | 11.63 |
| 4 | 2.4 | 76.09 | 13.04 | 10.87 |

The equilibraton products were all water soluble, functioned as profoamers in water and left no silicone oil film on the water when the foam dissipated.

From this example it will be readily understood by those of ordinary skill in the silicone technology that carboxyfunctional silicone glycols comprising a wide variety of ratios of carboxyfunctional siloxane units, silicone glycol units and diorganosiloxane units can be made by the inventive method of the present invention.

EXAMPLE 3

This example demonstrates that carboxyfunctional silicone glycols having the structure of general formula (VI) can be made by the present inventive method from starting materials having structures according to general formulae (II) and (III). The carboxyfunctional siloxane and the acid catalyst used in this example are as in Example 1. The silicone glycol used in this example has the general formula

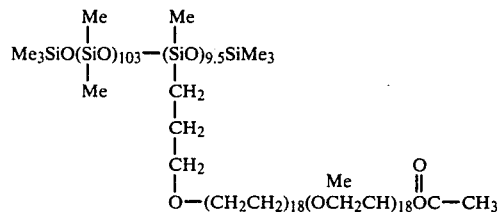

Three samples were made. Sample 5 was made from 2.1 grams of the carboxyfunctional siloxane of Example 1, 200 grams of the silicone glycol described above and 0.2 grams of trifluoromethane sulfonic acid. Sample 6 was the same as Sample 5 except that 4.0 grams of the carboxyfunctional siloxane was used. Sample 7 was the same as Sample 5 except that 8 grams of the carboxyfunctional siloxane was used.

The ingredients for Samples 5, 6 and 7 were each placed in a lightly capped bottle and heated to 65° C. The elevated temperature was maintained for 16 hours before the samples were cooled. Samples 5 and 6 were dark brown and clear with no precipitate. Sample 7 was yellow and fairly clear. All three samples were soluble in water where they functioned as profoamers. Standard laboratory analysis indicated that the samples conformed to general formula (VI).

The carboxyfunctional silicone glycols of this example have molar ratios of diorganosiloxane units, carboxyfunctional siloxane units and silicone glycol units as set out in Chart 3a.

| | Chart 3a | | |
|---|---|---|---|
| Sample | Mole % Diorganosiloxane Units | Mole % Carboxyfunctional Siloxane Units | Mole % Silicone Glycol Units |
| 5 | 90 | 1.6 | 8.4 |
| 6 | 89 | 3.0 | 8.0 |
| 7 | 86 | 6.0 | 8.0 |

From this example it will be readily understood by those of ordinary skill in the silicone technology that useful carboxyfunctional silicone glycols according to general formula (VI) can be made by the present inventive method in a variety of ratios of diorganosiloxane units, carboxyfunctional silicone units and silicone glycol units.

The present invention has been disclosed in the above teachings and examples with sufficient clarity and conciseness to enable one of ordinary skill in the silicone technology to make and use the invention, to know the best mode for carrying out the invention and to distinguish it from other inventions and from what is old.

What is claimed is:

1. A method for making a carboxyfunctional silicone glycol which method comprises the steps of:
   (1) mixing together
      (a) a silicone glycol or a mixture of silicone glycols in which at least one of the glycol radicals is bonded to silicon with an Si—C linkage;
      (b) a carboxyfunctional siloxane, or a mixture of carboxyfunctional siloxanes in which at least one of the carboxy radicals is bonded to silicon with an Si—C linkage wherein at least one of (a) and (b) also includes non-glycol-containing and non-carboxyfunctional-containing diorganosiloxane units; and
      (c) a catalytic amount of an acid catalyst capable of breaking Si—O linkages in (a) and (b) but incapable of breaking Si—C linkaqes therein;
   (2) heating the mixture to an elevated temperature; and
   (3) maintaining the mixture at said elevated temperature for at least about 4 hours, whereby equilibration of (a) and (b) occurs to produce an equilibration product containing carboxyfunctional silicone glycol.

2. The method of claim 1 wherein the mixing and heating steps are performed simultaneously.

3. The method of claim 1 wherein (c) is trifluoromethane sulfonic acid and wherein, in step (2), the mixture is heated to a temperature of from about 40° C. to about 65° C.

4. The method of claim 3 where (c) is present in the mixture in an amount of about 200 parts per million.

5. The method of claim 1 which includes the additional subsequent step of neutralizing acid catalyst (c) with a suitable base.

6. The method of claim 5 which includes the further subsequent step of filtering the treated equilibration product to remove salts produced by the neutralization of the acid catalyst.

7. The method of claim 3 which includes the additional subsequent step of neutralizing the trifluoromethane sulfonic acid with dimethyl formamid.

8. The method of claim 7 which includes the further subsequent step of filtering the equilibration product to remove salts produced by the neutralization of the trifluoromethane sulfonic acid catalyst.

9. The method of claim 1 including the additional subsequent step of reacting the carboxyfunctional silicone glycol in the equilibration product with a metal hydroxide to form the carboxylic acid salt of said glycol.

10. The method of claim 9 wherein the metal hydroxide is NaOH or KOH.

11. The method of claim 1 wherein (a) and (b) are present in amounts which will result in an equilibration product comprising from about 0.5 to about 20 mole percent carboxyfunctional siloxane units, and from about 0.5 to about 20 mole percent silicone glycol units.

12. The method of claim 1 wherein (a) is $R^3O(R^2O)_c(R'O)_b(CH_2)_aSiR_2(OSiR_2)_y(CH_2)_a(OR')_b(OR^2)_cOR^3$ wherein "y" is a positive integer, "R" is a substituted or unsubstituted hydrocarbon radical "R'" is —CH$_2$CH$_2$—, "R$^2$" is "R'" or $$-CH_2CH-,\atop \ \ \ \ \ |\atop \ \ \ \ \ CH_3$$

"R$^3$" is hydrogen or a substituted or unsubstituted hydrocarbon radical, "a" is a positive integer and "b" plus "c" either of which may be 0, are from about 1 to about 50, inclusive; or mixtures thereof, or $$R_3Si(OSiR)_w(OSiR_2)_zOSiR_3\atop |\atop (CH_2)_a\atop |\atop \left(\!\!{O\atop R'}\!\!\right)_b\atop |\atop \left(\!\!{O\atop R^2}\!\!\right)_c\atop |\atop O\atop |\atop R^3$$

wherein "w" and "z" are positive integers, and "R", "R'", "R$^2$", "R$^3$", "a", "b", and "c" are as described above, and (b) is $$[(R_3Si)(R_3SiO)]_e(SiO)_f\atop \ \ \ \ \ \ \ \ \ \ \ \ \ \ \ \ \ \ \ \ \ |\atop \ \ \ \ \ \ \ \ \ \ \ \ \ \ \ \ \ \ \ \ \ R^4COA\atop \ \ \ \ \ \ \ \ \ \ \ \ \ \ \ \ \ \ \ \ \ \|\atop \ \ \ \ \ \ \ \ \ \ \ \ \ \ \ \ \ \ \ \ \ O$$

wherein each "R" is as described above, "A" is hydrogen or any monovalent substituted or unsubstituted hydrocarbon radical, "R$^4$" is any divalent hydrocarbon radical or hetero-atom-containing hydrocarbon radical which provides Si—C linkage, "e" is 1 or 0, "f" is 3 to 6, inclusive, when "e" is 0, and "f" is a positive integer when "e" is 1; or $$R_3Si(OSiR_2)_j(OSiR)_hOSiR_3\atop |\atop R^4\atop |\atop C=O\atop |\atop O\atop |\atop A$$

wherein "R", "R$^4$" and "A" are as defined above and "j" and "h" are positive integers; or mixtures thereof.

13. The method of claim 12 wherein the carboxyfunctional silicone glycol in the equilibration product has the general formula:

$$R^3O(R^2O)_c(R'O)_b(CH_2)_aSiR_2(OSiR)_d(OSiR_2)_g(CH_2)_a(OR')_b(OR^2)_cOR^3\atop |\atop R^4\atop |\atop C=O\atop |\atop O\atop |\atop A$$

wherein "R", "R'", "R$^2$", "R$^3$", "R$^4$", "a", "b", "c" and "A" are as set out in claim 12 and the average molar ratio of "d" and "g" are selected such that the mole percent silicone glycol units and the mole percent carboxyfunctional siloxane units each varies from about 0.5 to about 20.

14. The method of claim 12 wherein the carboxyfunctional silicone glycol in the equilibration product has the general formula:

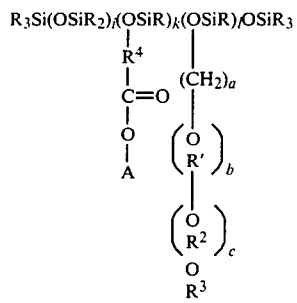

wherein "R", "R'", "R$^2$", "R$^3$", "R$^4$", "A", "a", "b", and "c" are as set out in claim 12 and wherein the average molar ratios of "i", "k" and "l" are selected such that the mole percent silicone glycol units and the mole percent carboxyfunctional siloxane units each varies from about 0.5 to 20.

15. The method of claim 13 wherein "A" is hydrogen and wherein the method includes the additional subsequent step of reacting the carboxyfunctional silicone glycol in the equilibration product with sodium hydroxide or potassium hydroxide whereby "A" is replaced by potassium or sodium to form the metal salt of the carboxyfunctional silicone glycol.

16. The method of claim 14 wherein "A" is hydrogen and wherein the method includes the additional subsequent step of reacting the carboxyfunctional silicone glycol in the reaction product with sodium hydroxide or potassium hydroxide whereby "A" is replaced by potassium or sodium to form the metal salt of the carboxyfunctional silicone glycol.

17. The method of claim 12 wherein R$^4$ is —CH$_2$CH$_2$SCH$_2$—.

18. The method of claim 13 wherein R$_4$ is —CH$_2$CH$_2$SCH$_2$—.

19. The method of claim 14 wherein R$_4$ is —CH$_2$CH$_2$SCH$_2$—.

* * * * *

UNITED STATES PATENT AND TRADEMARK OFFICE
CERTIFICATE OF CORRECTION

PATENT NO. : 4,587,320
DATED : May 6, 1986
INVENTOR(S) : Terence J. Swihart

It is certified that error appears in the above-identified patent and that said Letters Patent is hereby corrected as shown below:

In Col. 4, line 46, "interfer" should read --interfere--.

In Chart 2A, Heading Line, "Carboxyfunctional Siloxane" and "Silicone Glycol" are transposed.

In Col. 7, line 60, "$(OSiMe_2)$" should read -- $(OSiMe_2)_{15.5}$ --.

In Col. 7, line 61, "0.023" should read --0.0213--.

In Col. 9, line 37, "radios" should read --ratios--.

In Col. 11, line 21, "linkaqes" should read --linkages--.

In Col. 14, line 19, "$R_4$" should read --$R^4$--.

In Col. 14, line 21, "$R_4$" should read --$R^4$--.

Signed and Sealed this

Twenty-third Day of September 1986

[SEAL]

Attest:

DONALD J. QUIGG

Attesting Officer    Commissioner of Patents and Trademarks